(12) United States Patent
Cairns

(10) Patent No.: US 10,945,922 B1
(45) Date of Patent: Mar. 16, 2021

(54) APPARATUS FOR CREATING A SEALED CONDUIT BETWEEN SEPARATE VOLUMES

(71) Applicant: James L. Cairns, Ormond Beach, FL (US)

(72) Inventor: James L. Cairns, Ormond Beach, FL (US)

(73) Assignee: Abyssal Systems, Inc., Ormond Beach, FL (US)

( * ) Notice: Subject to any disclaimer, the term of this patent is extended or adjusted under 35 U.S.C. 154(b) by 0 days.

(21) Appl. No.: 16/583,941

(22) Filed: Sep. 26, 2019

(51) Int. Cl.
A61J 1/20 (2006.01)
A61M 39/10 (2006.01)
A61M 5/178 (2006.01)

(52) U.S. Cl.
CPC ............. A61J 1/2089 (2013.01); A61J 1/201 (2015.05); A61J 1/2051 (2015.05); A61M 5/1782 (2013.01); A61M 39/10 (2013.01)

(58) Field of Classification Search
CPC ....... A61J 1/1406; A61J 1/2089; A61J 1/2051
See application file for complete search history.

(56) References Cited

U.S. PATENT DOCUMENTS

| 3,986,508 | A | | 10/1976 | Barrington | |
| 4,080,965 | A | | 3/1978 | Phillips | |
| 4,387,879 | A | | 6/1983 | Tauschinski | |
| 4,430,081 | A | * | 2/1984 | Timmermans | A61M 39/0606 251/149.1 |
| 4,576,211 | A | * | 3/1986 | Valentini | A61J 1/2096 141/329 |
| 5,743,884 | A | | 4/1998 | Hasson et al. | |
| 6,033,426 | A | | 3/2000 | Kaji | |
| 6,089,541 | A | * | 7/2000 | Weinheimer | A61M 39/26 251/149.1 |
| 7,396,051 | B2 | * | 7/2008 | Baldwin | A61M 39/26 285/354 |
| 7,722,575 | B2 | | 5/2010 | Lopez | |
| 8,753,317 | B2 | | 6/2014 | Osborne et al. | |
| 9,414,991 | B2 | * | 8/2016 | Sanders | A61J 1/18 |
| 9,933,094 | B2 | * | 4/2018 | Fangrow | A61M 39/18 |

(Continued)

FOREIGN PATENT DOCUMENTS

| GB | 899807 A * | 6/1962 | ......... B65D 47/2031 |
| WO | 2005041846 A2 | 5/2005 | |
| WO | 2018129042 A1 | 7/2018 | |

OTHER PUBLICATIONS

U.S. Pat. No. 787,348, Apr. 11, 1905, E. J. Hansen (cited here because the patent section of this form-fillable will not accept this patent number).

(Continued)

Primary Examiner — Catharine L Anderson
Assistant Examiner — Arjuna P Chatrathi
(74) Attorney, Agent, or Firm — Mark T. Vogelbacker

(57) ABSTRACT

An apparatus for creating a sealed conduit between separate volumes includes a first unit and a second unit. The first unit includes a housing defining a first volume, a conduit, and at least one first penetrable interface. The at least one first penetrable interface is reconfigurable from a closed, sealed, condition when not penetrated by the conduit to a sealed condition with the conduit passing therethrough when penetrated by the conduit. The second unit includes a housing defining a second volume and at least one second penetrable interface.

13 Claims, 7 Drawing Sheets

(56) References Cited

U.S. PATENT DOCUMENTS

| | | | |
|---|---|---|---|
| 2003/0176847 A1* | 9/2003 | Hurst | A61J 1/067 |
| | | | 604/415 |
| 2004/0126742 A1 | 7/2004 | Heasley | |
| 2006/0276770 A1* | 12/2006 | Rogers | A61J 1/2089 |
| | | | 604/414 |
| 2010/0063364 A1 | 3/2010 | Bonadio et al. | |
| 2011/0022068 A1 | 1/2011 | Aighamdi | |
| 2011/0313368 A1 | 12/2011 | Weaver et al. | |
| 2014/0261877 A1 | 9/2014 | Ivosevic et al. | |
| 2015/0141937 A1* | 5/2015 | Bonaldo | A61M 39/26 |
| | | | 604/256 |
| 2018/0193627 A1* | 7/2018 | Cairns | A61M 39/0606 |
| 2018/0200147 A1 | 7/2018 | Sanders | |

OTHER PUBLICATIONS

Notice from the Search Authority for International Patent Application No. PCT/US2018/012184 dated Mar. 6, 2018.
International Search Report and Written Opinion for International Patent Application No. PCT/US2018/012184 dated May 1, 2018.
International Search Report and Written Opinion dated Dec. 4, 2020 for PCT Application No. PCT/US2020/052074.

* cited by examiner

APPARATUS FOR CREATING A SEALED CONDUIT BETWEEN SEPARATE VOLUMES

FIELD

Embodiments of the presently disclosed technology relate to a reusable apparatus for sealably passing one or more elongated objects, optionally in the form of medical instruments or tubular conduits, from one volume into another volume wherein both volumes can remain sealed from the ambient or external environment, and wherein the passage of other objects or fluids into or out of the volumes is prevented during and after use. The presently disclosed technology allows an interface portion of the housing of one volume to be joined to an interface portion of the housing of a second volume in such a way that the joined interfaces can be sealable penetrated with a tubular conduit through which material (e.g., fluid) can pass between the volumes.

Some of the potential applications of the presently disclosed technology are herein described for the field of medicine, although it will be clear that uses for the disclosed technology go far beyond that field.

BACKGROUND

There are many practical applications requiring a conduit to be formed between separate volumes while otherwise maintaining the volumes sealed from the outside environment. For example, sometimes fluids must be repeatedly injected or withdrawn from a patient, requiring a sealed connection, such as at the junction between an injection device and the conduit where fluids are introduced into the patient. Some require the sealed connector portion on the patient to remain in place in order to be joined over and over to one or more other volumes. Still other attributes of such sealed interfaces are that, for purposes of repeated patient intervention, they must be reliable, reusable, and easily disinfected between uses.

Presently available technology offers a variety of means to address medical applications such as that described above; however, there are some ubiquitous disadvantages to the existing art. Many prior art devices use one or more elastomeric barriers puncturable by sharp spikes or hypodermic needles, such as illustrated in U.S. Pat. Nos. 3,986,508, 4,080,965, and 7,722,575. Elastomeric barriers that are perforated by hypodermic needles for instance, are not only dangerous to practitioners, but are degraded with each use. So their reliable reuse is not guaranteed. Another disadvantage of prior-art devices is their relative complexity, which makes them expensive, difficult to manufacture, and hard to clean. Some employ one or more stacked, linearly slitted elastomeric seals in various configurations such as described in U.S. Pat. Nos. 4,387,879, 5,743,884, 6,033,426, and US 2010/0063364. Seals with linear slits are problematic at least because they do not always snap closed immediately due to weak restoring forces supplied only by the tendency of the slits to return elastically to the closed position, and they do not seal well to cylindrical objects inserted through them. Linear slits result in eye-shaped openings whose extremes do not conform to inserted cylindrical objects. So linear slits do not always seal tightly, and if there is a pressure differential across linear slits, it results in leakage past the interface. Stacking slitted seals does not completely solve the leakage associated with the nonconformity.

None of the abovementioned prior art sealed interface structures is ideal due to the reasons stated. Many medical devices of this general sort are used once and then discarded, so expense is an important factor favoring simple, economical products.

SUMMARY

Noting the shortcomings of existing art, it's clear that volumes having sealed, uncomplicated, interfaces that are reliable, easily and rapidly penetrated, easily cleanable, reusable through many uses, remain sealed from the outside environment during and after use, and that can remain sealed up to a chosen differential pressure, would be very useful in many medical procedures, as well as in other applications.

The interfaces of at least one embodiment of the presently disclosed technology can include elastomeric barriers that permit sealable insertion of an object, such as an elongated tube, through them, and that return to sealed, dosed conditions when the object is withdrawn. The barriers can include a movable segment, optionally in the form of a crescent shaped perforation cut completely therethrough. No material needs to be removed from the barrier when the crescentric cut is made. The perforation can define a plug-like element, hereinafter called the tap, and a bore. Both the tap and bore can remain integral portions of the barrier, hereinafter referred to also as the seal or interface. The tap can remain sealably closed and in the bore when no object is inserted through the bore, and can distort to unseat from the bore when the bore is penetrated by an elongated object. During withdrawal of the object, the tap can return immediately to its seat and, in the process, be at least slightly compressed as it is moved back into the bore such that the tap can "squeegee" the bore clean. This one-piece construction eliminates many of the complexities of existing penetrable interfaces while satisfying the desired attributes of reliability, ease and rapidity of penetration and disinfecting, reusability, and remaining sealed up to a preset differential pressure both during penetration, when penetrated, and after the penetrating object is withdrawn.

In one embodiment, the presently disclosed technology is directed to an apparatus configured to sealably connect two or more volumes. Each volume can include a housing having one or more elastomeric interface portions wherein the interface portions can comprise an elastomeric barrier including a seal. The seal can include a first segment and a second segment. A portion of the second segment can be integrally formed with a portion of the first segment. The first and second segments can create a sealing engagement therebetween in the absence of an applied force such as might be applied by a rigid object or by a pre-determined differential pressure acting against the second segment. The first and second segments can be distorted out of sealing engagement when subjected to an applied force on the second segment. The elastomeric interface portions of separate volumes can be pressed together to seal their joined interfaces from the external environment. The joined interfaces can then be penetrated for example by a tubular element thereby forming a sealed conduit from one volume into the other.

BRIEF DESCRIPTION OF THE DRAWINGS

The presently disclosed technology is presented herein in general terms without regard to any specific application. It will be easily understood that the described apparatus can be readily adapted to a wide variety of housings, sizes, materials, and/or exterior configurations, making it adaptable to a broad spectrum of applications. The presently disclosed technology's salient features and advantages will become readily apparent to those of ordinary skill in the art after reviewing the following detailed description in light of the accompanying drawings, in which like reference numbers refer to like parts, and in which.

DETAILED DESCRIPTION

Figure 1:
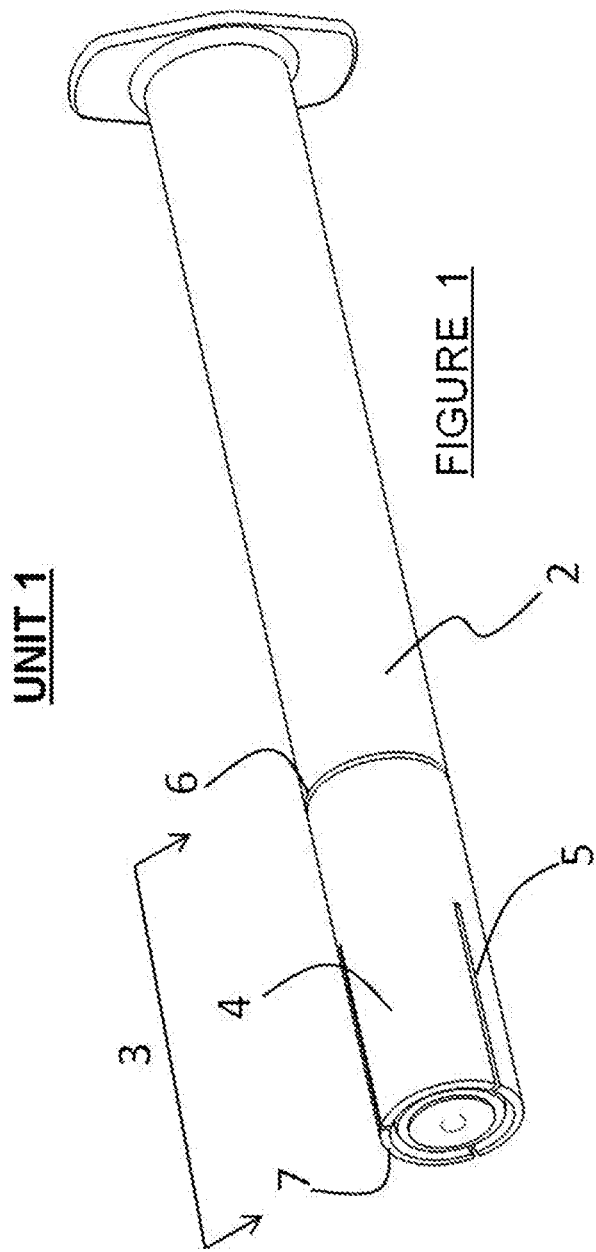
FIG. 1 is an isometric view of a first unit or Unit 1 of a device of one embodiment of the presently disclosed technology.

Certain terminology is used in the following description for convenience only and is not limiting. The words "forward" and "rearward" (and derivations thereof) designate directions in the drawings to which reference is made. Unless specifically set forth herein, the terms "a," "an" and "the" are not limited to one element but instead should be read as meaning "at least one." The terminology includes the words noted above, derivatives thereof and words of similar import.

For purposes of clarity and brevity, the present description designates one of the units configured to be joined as Unit 1, wherein Unit 1 is a first unit that contains Volume A, and the other Unit 2, wherein Unit 2 is a second unit that contains Volume B. In operation, an open conduit or other object can sealably extend between Unit 1 and Unit 2 thereby connecting Volumes A and B.

The operation of the presently disclosed technology when used to permit insertion of elongated objects, for example, therethrough, will now be described in detail. A generic rendition of Unit 1 is illustrated in FIG. 1. Unit 1 includes housing 2, which is represented as an example therein simply as a medical syringe, but it is understood that it could be any appliance configured to sealably and mechanically attach to mating assembly 3. Unit 1 can include housing 2 and mating assembly 3, where housing 2 and mating assembly 3 can be optionally fixedly or permanently attached. The housing of mating assembly 3 includes tubular section 4 having optional spaced-apart axial slots 5, rear end wall 6 and forward end wall 7.

Figure 2:
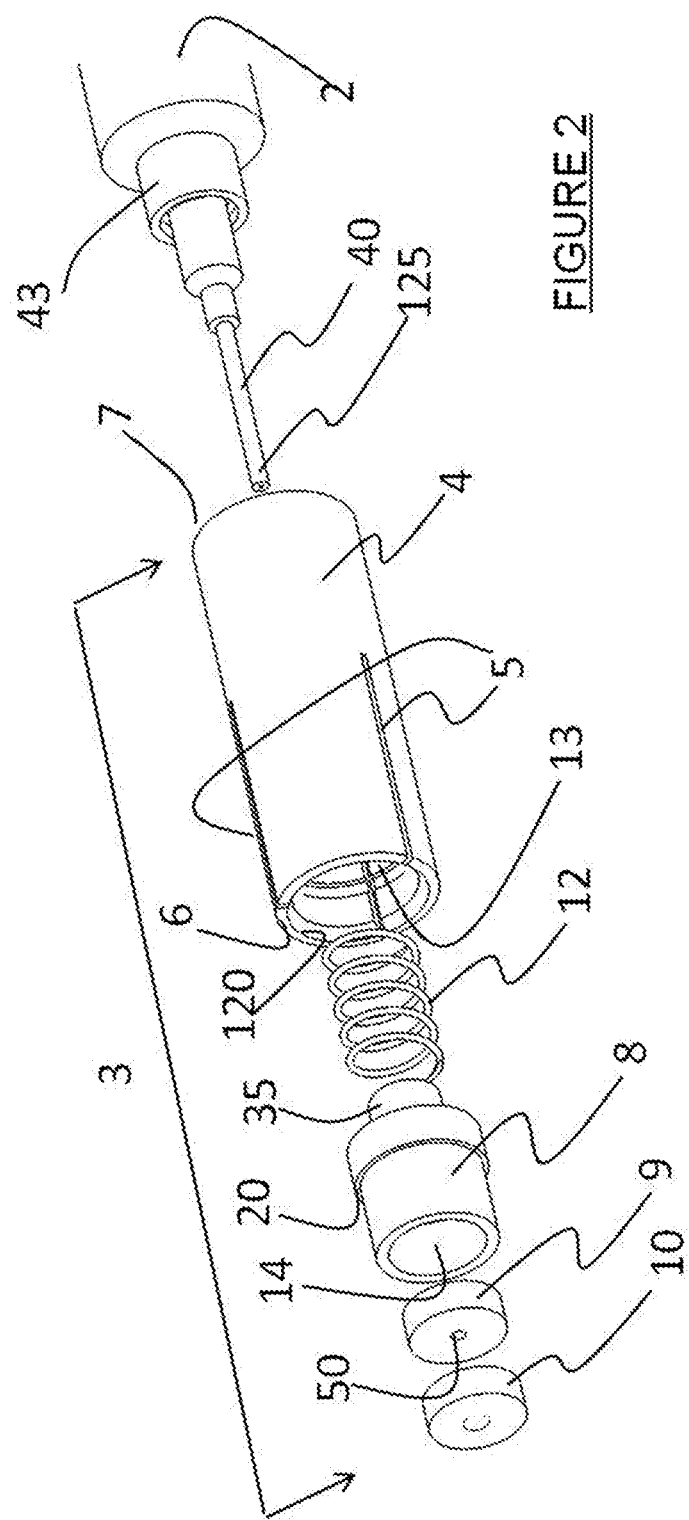
FIG. 2 is an isometric exploded view of at least a mating assembly of Unit 1 of the device in an unmated condition.

FIG. 2 shows an axially exploded view of an exemplary mating assembly 3 with its various components arranged in the order in which they can be assembled. Movable carriage 8 can house inner elastomeric seal 9 and elastomeric interface 10 within seat 14. Movable carriage 8 along with incorporated inner seal 9 and elastomeric interface 10 can be assembled along with spring 12 into tubular section 4 through open end 13 of tubular section 4. Axial slots 5 in tubular section 4 can allow open end 13 of tubular section 4 to be forcibly expanded or sprung open sufficiently by the entrance of movable carriage 8 to permit movable carriage 8 to enter tubular section 4.

Figure 3:
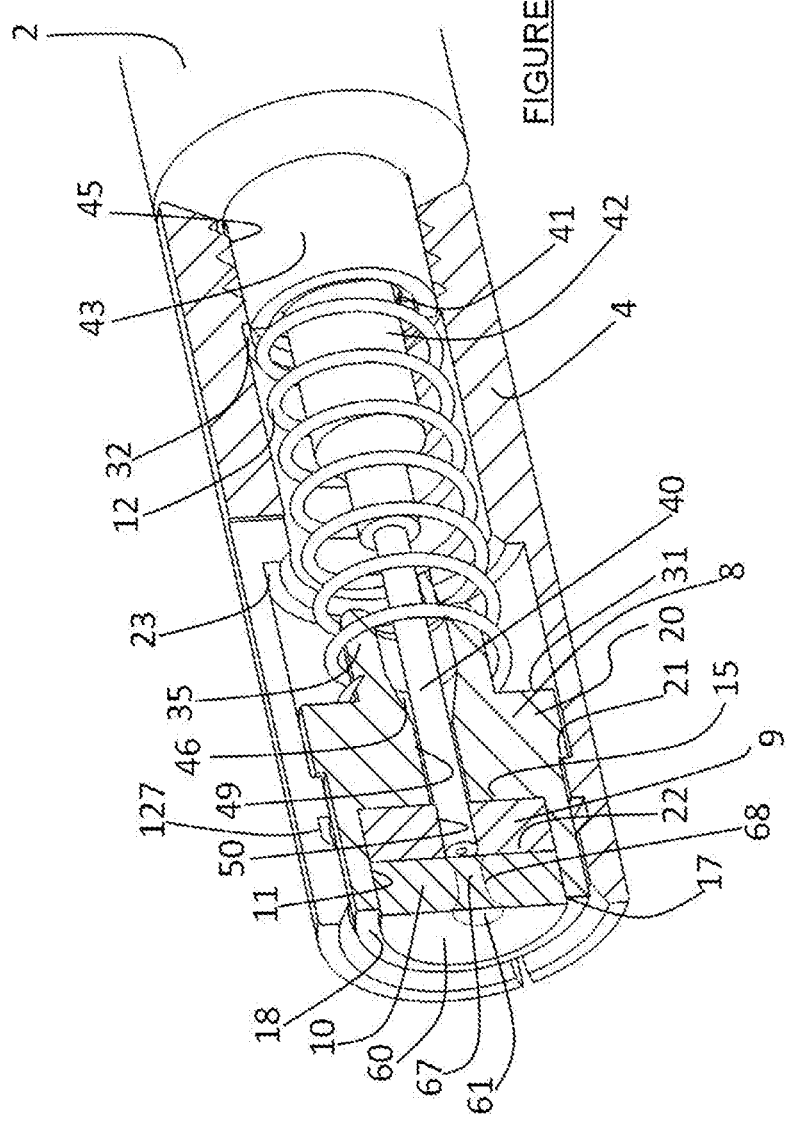
FIG. 3 is an axial partially cutaway isometric view of the mating assembly of Unit 1 of the device in the unmated condition.

FIG. 3 illustrates a partial axial cutaway of mating assembly 3. Inner elastomeric seal 9 can be captured against movable carriage rear wall 15 on its rearward end, and against elastomeric interface 10 on its forward end. Elastomeric interface 10 can be captured on its rearward end by elastomeric seal 9. Both elastomeric seal 9 and elastomeric interface 10 can be adhesively (or otherwise) fixed to inner wall 11 of seat 14 of movable carriage 8. Front portion 17 of elastomeric interface 10 can protrude outwardly slightly beyond end wall 18 of movable carriage 8. Forward travel (i.e., leftward in FIG. 3) of movable carriage 8 within tubular section 4 of mating assembly 3 can be stopped when larger diameter portion 20 or an extension portion of movable carriage 8 butts against shoulder 21 of tubular section 4. Rearward travel (i.e., rightward in FIG. 3) of movable carriage 8 can be stopped when larger diameter portion 20 of movable carriage 8 butts against shoulder 23 of tubular section 4.

Movable carriage 8 can be urged forward within tubular section 4 by compression spring 12 or another type of biasing member. Spring 12 can be assembled in a partially compressed state thereby providing a preload to keep movable carriage 8 urged forward against shoulder 21 of tubular section 4. Spring 12 can act against rear wall 31 of movable carriage 8 and against shoulder 32 of tubular section 4. Smaller rear diameter portion 35 of movable carriage 8 can serve as a squirm guide for compression spring 12.

Looking now at FIGS. 2 and 3, during the assembly of mating assembly 3, once larger diameter portion 20 of movable carriage 8 has moved inwardly beyond shoulder 21 of tubular section 4, open end 14 can spring radially inwardly thereby capturing all of the components of mating assembly 3 within tubular section 4. Axial slots 5 can serve to permit ventilation of the inner portions of tubular section 4 to the outside environment.

In one exemplary embodiment, conduit or industrial dispensing needle 40 having male Luer-lock threads 41 on rear portion 42 can be sealably threaded into forward portion 43 of syringe body or housing 2. Dispensing needles such as 40 have blunted tips, and therefore pose no needle-stick risk to practitioners.

In one optional embodiment, during the assembly of Unit 1, dispensing needle 40 can first be installed onto syringe body 2. Next, pre-assembled mating assembly 3 can be (e.g., mechanically) attached to syringe body 2, for example by advancing threads 45 of tubular section 4 onto portion 43 of syringe body 2. Forward portion 43 of syringe body 2 need not have threads to mate to threads 45 of tubular section 4. Threads 45 can bite into forward portion 43 of tubular section 4 with enough holding strength to keep mating assembly 3 firmly in place on syringe body 2. Tapered bore segment 46 in the rear of movable carriage 8 can assist during assembly of mating assembly 3 onto syringe body 2 by guiding dispensing needle 40 into smaller through-bore 49 of movable carriage 8 and thence into bore 50 of inner elastomeric seal 9.

Through-bore 49 of inner elastomeric seal 9 can sealably stretch slightly over the outer diameter of industrial needle 40, thereby forming a seal to the outer diameter of needle 40. When assembled as just described, Volume A within syringe 2 can be sealed on its forward end by mating assembly 3.

Figure 4:
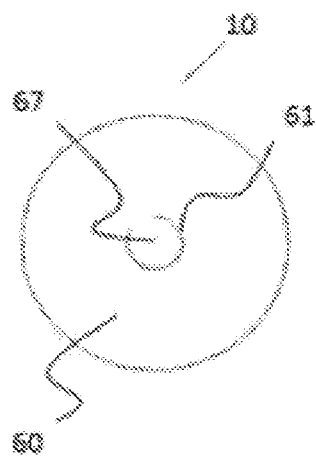
FIG. 4 is a face view of one embodiment of an elastomeric interface of Unit 1.
Figure 5:
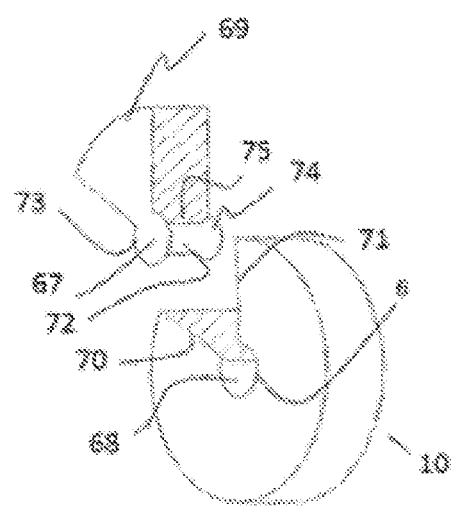
FIG. 5 is an oblique view of the interface of FIG. 4 shown sectioned for purposes of illustration only.

Elastomeric interface 10 is shown in greater detail in the views depicted in FIGS. 4 and 5. Interface 10 is shown therein as a cylindrical object, but Interface 10 can take the form of virtually any shape. The front elevation view of Interface 10 in FIG. 4 shows on a first portion or face 60, with the outline of perforation 61, which can form a crescent-shape. However, perforation 61 can form other shapes. Perforation 61 cuts axially through the entire thickness of interface 10, not necessarily with a circular or uniform diameter, thereby resulting in second portion or tap 67, and bore 68. Thus, face 60 and tap 67 are integrally or monolithically formed, but are configured to be distorted out of position with respect to each other without compromising the connection therebetween.

Interface 10 and its integral parts are easier to visualize by the oblique view of FIG. 5 in which, for purposes of better understanding, a portion 69 is shown cut away axially from interface 10 along lines 70, 71 which radiate outwardly from the ends of crescentric perforation 61. In FIG. 5, cutaway portion 69 is shown displaced radially outward from the remainder of interface 10 for clarity and purpose of illustration only. Tap 67 can include central portion 72 having first flared segment 73 on one end, and another or second flared segment 74 on the other or opposite end of central portion 72. In one embodiment, tap 67 remains attached to the main portion of interface 10 by uncut portion 75 of perforation 61. Uncut portion 75 provides a substantial elastic force to return tap 67 to its at-rest or initial position within bore 68 in the absence of externally applied forces. In one embodiment, flared end segments 73, 74 (FIG. 5) of tap 72 aid in centering the tap axially within bore 68, and enhance both the wiping and sealing functions of the tap.

In FIGS. 4 and 5 interface 10 is shown not activated or opened; tap 67 is seated within bore 68, thereby preventing the flow of fluid through the bore 68 in the absence of an applied force on interface 10. Referring to FIG. 3, industrial dispensing needle 40 is shown in position ready to forcibly penetrate the sealed barrier via bore 68. Further details of interface 10 are shown in FIGS. 2-5 and described in paragraphs [0025], [0026], and [0028]-[0035] of U.S. Publication No. 2018/0193627 (Cairns), these specific portions of that publication are hereby incorporated by reference.

Figure 6:
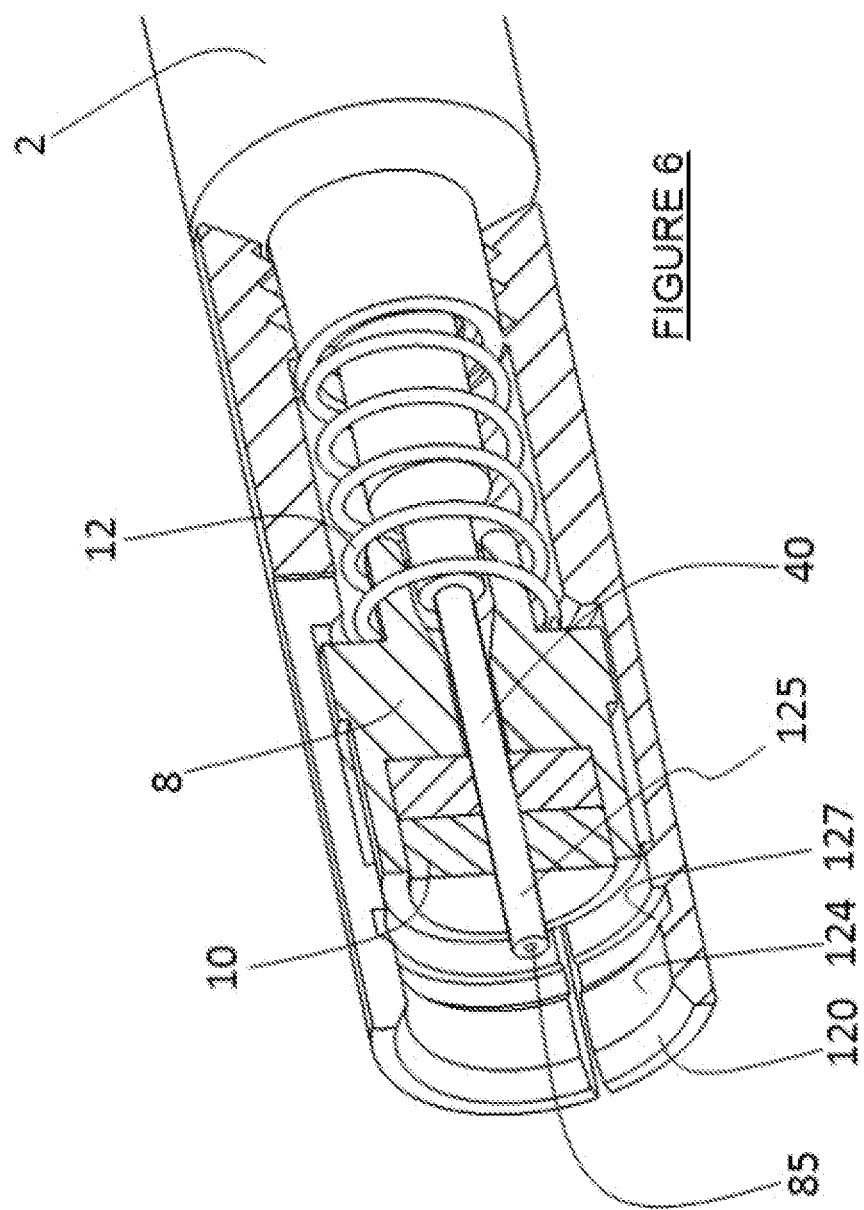
FIG. 6 is an axial partially cutaway isometric view of the mating assembly of the first unit of the device as it would appear in the mated condition.

FIG. 6 illustrates one embodiment of the condition wherein movable carriage 8 has been forced inwardly further compressing spring 12. Dispensing needle 40 has penetrated interface 10 thereby unsealing passageway 85 of dispensing needle 40, and thereby connecting Volume A within syringe 2 (see FIG. 8) through passageway 85 of needle 40 to the exterior environment of the syringe 2.

Figure 7:
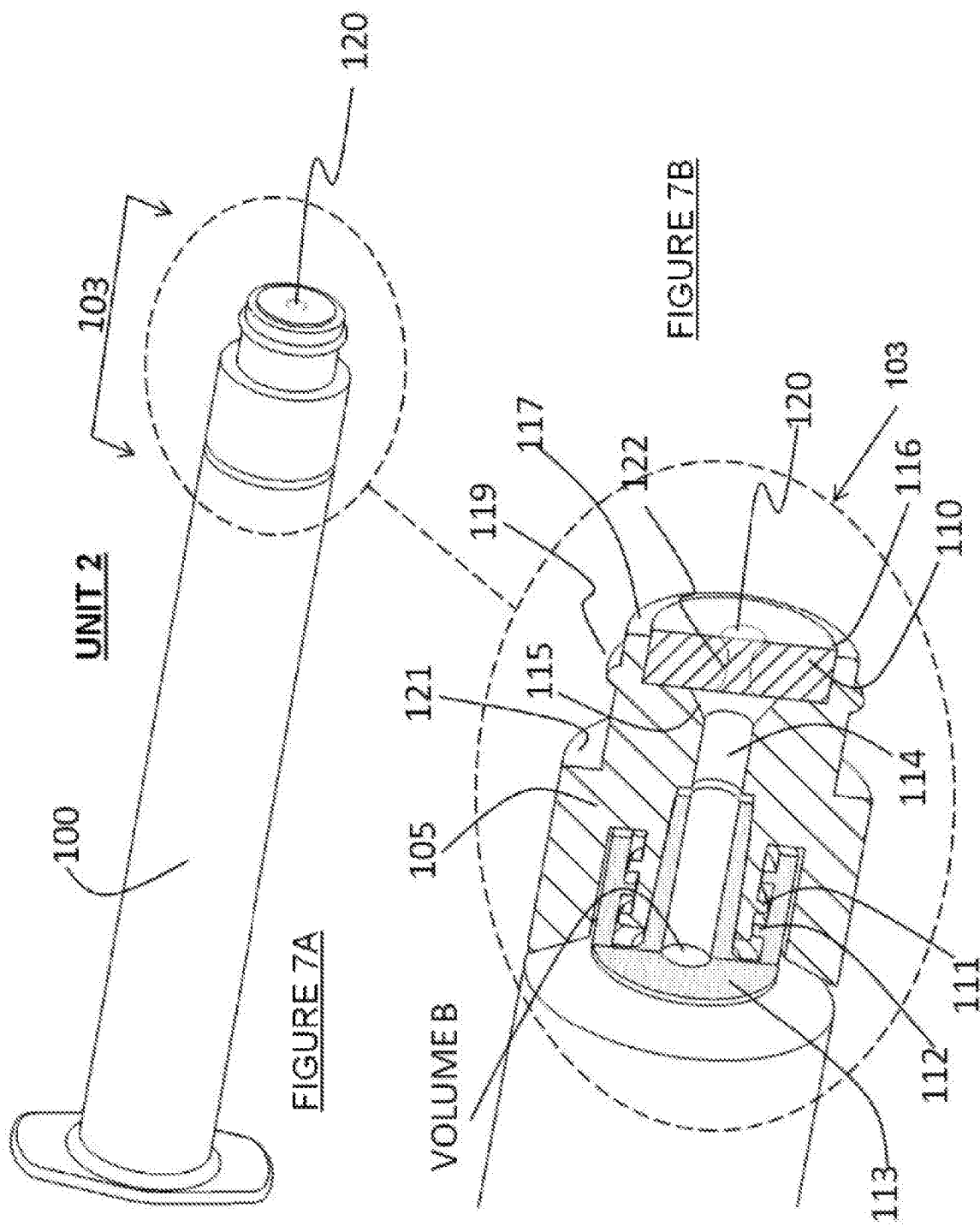
FIG. 7A is an isometric view of a second unit or Unit 2 of the device of one embodiment of the presently disclosed technology.
FIG. 7B is an enlarged section of at least a mating assembly of Unit 2.

An exemplary, generic rendition of Unit 2 is illustrated FIGS. 7A and 7B. Unit 2 includes housing 100, which is represented therein simply as a medical syringe, but it is understood that it could be any appliance configured to sealably and mechanically attach to mating assembly 103. Unit 2 can include housing 100 and mating assembly 103, where both components are optionally fixedly or permanently attached.

Mating assembly 103 can include two components: housing 105 and interface 110. The rearward (e.g., leftward in FIG. 7B) portion of housing 105 can optionally have male Luer-lock threads 111 that sealably thread onto female Luer-lock threads 112 shown on partially cut-away forward portion 113 of syringe 100. Though other connection means are possible.

Interface 110 can be of similar or identical tap-and-bore construction to that of interface 10 of Unit 1, including tap 120 and bore 122. Housing 105 can have through bore 114, which can extend from just within interface 110 into Volume B within syringe 100. Tapered portion 115 of bore 114 allows space for tap 110 to distort inward when penetrated by an elongated object, such as but not limited to industrial needle 40 of Unit 1. Tapered portion 115 of bore 114 can also serve to align a penetrating object, such as industrial needle 40, with bore 114 upon being penetrated by that object. A portion 116 of interface 110 can extend beyond outwardly beyond forward face 117 of housing 105.

Figure 8:
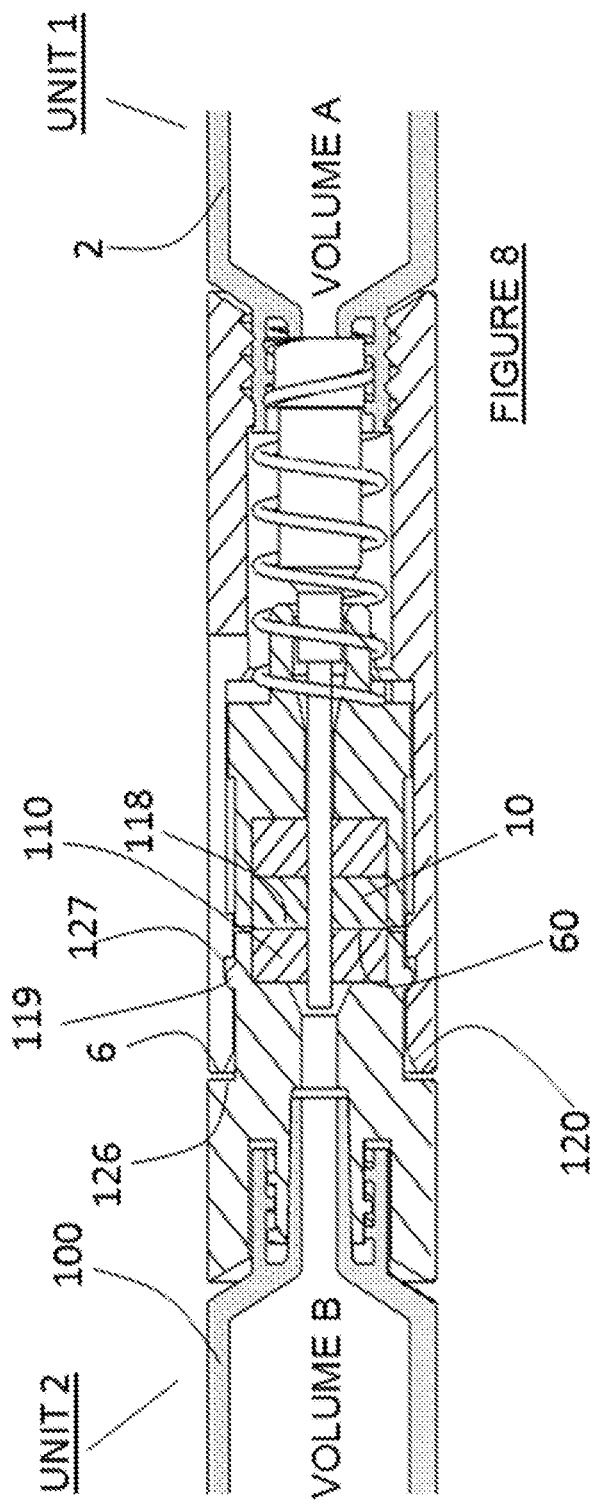
FIG. 8 is an axial cross-sectional view of the mated Units 1 and 2 showing a volume within each of first and second units (Volumes A and B) connected by an open conduit.

FIG. 8 shows one embodiment wherein Unit 1 and Unit 2 are fully engaged.

As Unit 1 and Unit 2 begin to engage, they are first aligned axially. As engagement proceeds, face 60 of interface 10 of Unit 1 can engage or contact face 118 of interface 110 of Unit 2. Both faces 60 of interface 10 and face 118 of interface 110 can protrude at least slightly outwardly (17, 116) from their seats in movable carriage 8 and housing 105, respectively, to insure that the point of face-to-face contact between Unit 1 and Unit 2 is between interfaces 10, 110, and not between end face 18 (FIG. 3) of moveable carriage 8 of Unit 1 and forward face 117 (FIG. 7B) of housing 105 of Unit 2. Further insertion of Unit 2 into Unit 1 can proceed by overcoming the force needed to further compress spring 12. Deeper insertion of Unit 2 into Unit 1 can cause annular nib 119 (FIG. 7B) of housing 105 to forcibly move against lead-in taper 120 (FIG. 2) of tubular section 4, thereby at least slightly expanding open end 13 of tubular section 4 radially outward permitting housing 105 to pass into bore 124 (FIG. 8) of tubular section 4.

Penetration of Unit 2 into Unit 1 can cause engaged interfaces 10, 110 to be sealably pressed together with an axial force provided by the preload and additional compression of spring 12. Further engagement can cause pressed together interfaces 10, 110 to move inwardly (e.g., rightward in FIG. 8) relative to tubular section 4 of Unit 1, and thereby can cause tip 125 of dispensing needle 40 to pass through interfaces 10, 110 and onward into bore 114 (FIG. 7B) of housing 105. Engagement can proceed until housing 105 of mating assembly 103 of Unit 2 has moved inwardly within tubular section 4 of Unit 1 to the point where forward wall 6 of tubular section 4 of Unit 1 meets wall 126 (FIG. 8) of housing 105 mating assembly 103 of Unit 2. At that point, annular nib 119 of housing 105 can be engaged and/or positioned in seat 127 of tubular section 4. The force provided by compressed spring 12 is directed to urge engaged Units 1 and 2 apart; however, the engagement of annular nib 119 within seat 127 can be adequate to keep the units engaged and thereby overcome the force provided by spring 12.

Both interface 10 and interface 110 can be closed, smooth, and accessible when Unit 1 and Unit 2 are disengaged, and therefore are easily disinfected between uses.

Disengagement of Unit 1 from Unit 2 is the reverse of the engagement sequence outlined above.

In one embodiment, the above-described features of the presently disclosed technology allow for the transfer of material (such as but not limited to fluid or powder) between two sealed volumes, wherein each volume remains sealed before, during and after transfer. However, the volumes are not necessarily closed. In one embodiment, one or each volume can be open on its rearward portions, for example. If one or each volume were a tube or a hose, instead of a syringe, the hose could be open at one end.

The above description of generic embodiments of the presently disclosed technology is provided to enable any person skilled in the art to make or use the presently disclosed technology. Various modifications to the embodiments will be readily apparent to those skilled in the art, and the generic principles described herein can be applied to other embodiments without departing from the spirit or scope of the presently disclosed technology. Thus, it is to be understood that the description and drawings presented herein represent a functional generic embodiment of the presently disclosed technology and are therefore representative of the subject matter which is broadly contemplated by the presently disclosed technology. It is further understood that the scope of the presently disclosed technology fully encompasses other embodiments that would become apparent to those skilled in the art and that the scope of the presently disclosed technology is accordingly limited by nothing other than the appended claims.

What is claimed is:

1. An apparatus for creating a sealed conduit between separate volumes, the apparatus comprising:

a first unit having a housing defining a first volume, a conduit, and at least one first elastomeric seal having a crescentric cut formed axially through at least a portion of the first elastomeric seal during manufacture of the first elastomeric seal, the crescentric cut defining a first segment in the form of a bore that is positioned radially outward of the crescentric cut and a second segment in the form of a tap that is positioned radially inward of the crescentric cut, the first and second segments being a monolithic unit with the crescentric cut extending therethrough, the tap remains attached to a main portion of the first elastomeric seal by an uncut portion of the crescentric cut, the first and second segments creating a sealing engagement therebetween in the absence of an applied force on the second segment, the first and second segments being distorted out of sealing engagement when subjected to an applied force on the second segment, the uncut portion providing an elastic force to return the tap to an at-rest position within the bore in the absence of an applied force, the at least one first elastomeric seal being reconfigurable from a closed, sealed, condition when not penetrated by the conduit to a sealed condition with the conduit passing therethrough when penetrated by the conduit, and a second unit having a housing defining a second volume and at least one second elastomeric seal, wherein the at least one second elastomeric seal of the second unit is sealed when not engaged with the first elastomeric seal of the first unit, and is opened when sealably engaged with the first elastomeric seal and penetrated by the conduit of the first unit, the second elastomeric seal having a crescentric cut formed axially therethrough during manufacture of the second elastomeric seal, the crescentric cut of the second elastomeric seal defining a first segment in the form of a bore that is positioned radially outward of the crescentric cut and a second segment in the form of a tap that is positioned radially inward of the crescentric cut, the first and second segments of the second elastomeric seal being a monolithic unit with the crescentric cut extending therethrough, the tap remains attached to a main portion of the second elastomeric seal by an uncut portion of the crescentric cut, the first and second segments of the second elastomeric seal creating a sealing engagement therebetween in the absence of an applied force on the second segment, the first and second segments being distorted out of sealing engagement when subjected to an applied force on the second segment, the uncut portion providing an elastic force to return the tap to an at-rest position within the bore in the absence of an applied force, the second elastomeric seal being reconfigurable from a closed, sealed, condition when not penetrated by the conduit to a sealed condition with the conduit passing therethrough when penetrated by the conduit, wherein the first and second elastomeric seals are configured to be pressed together to form a seal therebetween with respect to an external environment, and wherein the first unit includes a third elastomeric seal having a rearward end, a forward end, and a throughbore, the rearward end of the third elastomeric seal contacting a rear wall of a portion of the apparatus, and the forward end of the third elastomeric seal contacting the first elastomeric seal.

2. The apparatus of claim 1, wherein the first unit includes a biasing member, the biasing member being configured to urge the first elastomeric seal toward the second elastomeric seal.

3. The apparatus of claim 1, wherein the first unit includes a mating assembly having a carriage movable within a tubular section of the mating assembly, the first elastomeric seal being configured to fit within a portion of the movable carriage.

4. The apparatus of claim 3, wherein the carriage is movable with respect to the tubular section such that at least a tip of the conduit extends past the first elastomeric seal when the carriage is moved a sufficient distance with respect to the first volume, and wherein the tip of the conduit does not cut, tear, or otherwise mar the first elastomeric seal.

5. The apparatus of claim 1, wherein the second segment of the first elastomeric seal includes a first flared portion.

6. The apparatus of claim 5, wherein the second segment of the first elastomeric seal includes a second flared portion spaced-apart from the first flared portion.

7. The apparatus of claim 1, wherein the housing of the first unit is a syringe.

8. The apparatus of claim 1, wherein the conduit has a blunt front end.

9. The apparatus of claim 1, wherein the second unit includes the housing and a mating assembly, wherein a rearward portion of the mating assembly of the second unit includes Luer-lock threads configured to sealably thread onto Luer-lock threads of the housing of the second unit.

10. The apparatus of claim 1, wherein a through bore is formed axially through a portion of the first elastomeric seal during manufacture of the first elastomeric seal, the through bore being aligned with and in series to the crescentric cut of the first elastomeric seal.

11. An apparatus for creating a sealed conduit between separate volumes, the apparatus comprising:

a first elastomeric seal a second elastomeric seal, and a third elastomeric seal, the first and second elastomeric seals being configured to be pressed together to form a seal therebetween with respect to an external environment, the first and second elastomeric seals being configured to allow passage of a conduit therethrough to permit material to flow from one of two separate volumes to the other of the two separate volumes without passage to the external environment, wherein the conduit has a blunt front end and does not cut, tear, or otherwise mar either the first or second elastomeric seals upon passage therethrough, wherein a perforation cuts axially through an entire thickness of each of the first and second elastomeric seals thereby resulting in a tap and a bore in each of the first and second elastomeric seals, the tap remains attached to a main portion in each of the first and second elastomeric seals by an uncut portion of the perforation, the uncut portion of each of the first and second elastomeric seals providing an elastic force to return the respective tap to an at-rest or initial position within the respective bore in the absence of an applied force, and wherein the third elastomeric seal has a rearward end, a forward end, and a through-bore, the rearward end of the third elastomeric seal contacting a rear wall of a portion of the apparatus, and the forward end of the third elastomeric seal contacting the first elastomeric seal.

12. The apparatus of claim 11, wherein the first elastomeric seal is at least partially enclosed within a housing, wherein the housing includes a biasing member configured to urge the first elastomeric seal toward and into contact with the second elastomeric seal.

13. The apparatus of claim 11, wherein the first elastomeric seal sealingly closes a first volume when the conduit does not penetrate the first elastomeric seal, and wherein the second elastomeric seal sealingly closes a second volume when the conduit does not penetrate the second elastomeric seal.

* * * * *